United States Patent

Kasic, II et al.

(10) Patent No.: US 6,491,622 B1
(45) Date of Patent: Dec. 10, 2002

(54) APPARATUS AND METHOD FOR POSITIONING IMPLANTABLE HEARING AID DEVICE

(75) Inventors: James Frank Kasic, II, Boulder, CO (US); Douglas Alan Miller, Lafayette, CO (US); Jose H. Bedoya, Boulder, CO (US)

(73) Assignee: Otologics LLC, Boulder, CO (US)

( * ) Notice: Subject to any disclaimer, the term of this patent is extended or adjusted under 35 U.S.C. 154(b) by 0 days.

(21) Appl. No.: 09/583,299

(22) Filed: May 30, 2000

(51) Int. Cl.⁷ .............................................. H04R 25/00
(52) U.S. Cl. ........................................................ 600/25
(58) Field of Search .................... 600/25, 559; 128/897, 128/898; 607/55, 56, 57; 623/10; 606/130

(56) References Cited

U.S. PATENT DOCUMENTS

| | | | |
|---|---|---|---|
| 3,651,521 A | 3/1972 | Devas ................................. 3/1 |
| 4,281,419 A | 8/1981 | Treace ............................. 3/1.9 |
| 4,601,723 A | 7/1986 | McGrew ...................... 623/10 |
| 4,655,776 A | 4/1987 | Lesinski ....................... 623/10 |
| 4,922,333 A | 5/1990 | Nutting et al. ................. 358/78 |
| 5,024,224 A | 6/1991 | Engebretson ............ 128/420.6 |
| 5,085,628 A | 2/1992 | Engebretson et al. ......... 600/25 |
| 5,217,011 A | 6/1993 | Bisch ....................... 128/420.6 |
| 5,282,858 A | 2/1994 | Bisch et al. ................... 623/10 |
| 5,370,689 A | 12/1994 | Causse ......................... 623/10 |
| 5,562,737 A | 10/1996 | Graf ............................. 623/17 |
| 5,702,342 A | 12/1997 | Metzler et al. ............... 600/25 |
| 5,776,144 A | * 7/1998 | Leysieffer et al. ............. 600/25 |
| 5,788,711 A | * 8/1998 | Lehner et al. ................. 600/25 |
| 5,941,814 A | 8/1999 | Lehner et al. ................. 600/25 |
| 5,954,628 A | 9/1999 | Kennedy ....................... 600/25 |
| 5,993,376 A | 11/1999 | Kennedy ....................... 600/25 |
| 6,001,129 A | 12/1999 | Bushek et al. ................. 623/10 |
| 6,077,215 A | * 6/2000 | Leysieffer ..................... 600/25 |
| 6,113,531 A | * 9/2000 | Leysieffer et al. ............. 600/25 |

OTHER PUBLICATIONS

HNO Hals–Nasen–Ohren–Heilkunde, Kopf– und Hals–Chirurgie; Elektronische Horimplantate bei Innenohrschwerhorigkeiten; Springer; pp. A3–A5 and 737–880.

* cited by examiner

Primary Examiner—Kevin Shaver
Assistant Examiner—Brian Szmal
(74) Attorney, Agent, or Firm—Marsh Fischmann & Breyfogle LLP (57) ABSTRACT

The present invention is directed to an apparatus and method for supportably positioning an implantable hearing aid actuator within a patient's skull. The improved apparatus includes a carry device for carrying an implantable hearing aid actuator at a first end, a swivel device for pivotably supporting the carrier device, and a mounting device for mounting the apparatus to a patient's skull. To facilitate installation, a swivel device may be provided in a unitary manner so as to provide for selective placement and securement as a single unit to the mounting device. To yield enhanced depth positioning, the carrier device may be selectively advancable relative to the swivel device, and the carrier device may comprise two or more members interconnected for selective advancement of one relative to other. In the later regard, the carrier device may include at least a first member which telescopes coaxially relative to a second member.

37 Claims, 6 Drawing Sheets

APPARATUS AND METHOD FOR POSITIONING IMPLANTABLE HEARING AID DEVICE

FIELD OF THE INVENTION

The present invention relates to an apparatus and method for supportably positioning an implantable hearing aid actuator within a patient's skull, and more particularly, to a positioning apparatus and method that provides ease-of-installation, range-of-application, actuator loading and depth positioning advantages.

BACKGROUND OF THE INVENTION

Several types of implantable hearing aid devices have been proposed. Principally, such devices include those which utilize implanted electromechanical transducers for stimulation of the ossicular chain and/or oval window (see e.g., U.S. Pat. No. 5,702,342), and those which utilize implanted excitor coils to electromagnetically stimulate magnets affixed within the middle ear (see e.g., U.S. Pat. No. 5,897,486). For purposes hereof, such electromechanical transducers and excitor coils, as well other implanted devices that stimulate the ossicular chain and/or oval window will be collectively referred to as "implantable hearing aid actuators".

In most instances, hearing aid devices of the above-noted nature entail supportable positioning of the given implantable actuator within a patient's skull. In many procedures, an opening is surgically defined in a patients skull and the implantable actuator is inserted through the opening for supportable positioning within the mastoid process. In conjunction with such implant procedures, precise placement and orientation of the implantable actuator can be of paramount importance to achieve best results.

To yield precise positioning a number of arrangements have been proposed, wherein implantable actuator(s) may supportably disposed for selective in-site positioning in multiple dimensions relative to a skull mounting device. While such arrangements have represented an advance in the art, they often entailed the positioning of a number of separate, hard-to-handle components, thereby adding to the complexity already associated with implant procedures. Additionally, the present inventors believe that further enhanced positioning of implantable actuators is achievable, particularly with respect to the depth profile which can vary significantly from patient to patient.

SUMMARY OF THE INVENTION

In view of the foregoing, a primary objective of the present invention is to provide an apparatus and method for supportably positioning an implantable hearing actuator at a desired location with enhanced ease-of-installation. Additional objectives are to provide an implantation apparatus and method that yields enhanced accuracy in implantable hearing aid actuator positioning and/or range-of-application advantages. Yet a further objective of the present invention is to provide an apparatus and method that facilitates accurate, contact loading of an electromechanical transducer relative to a patient's ossicle.

One or more of the above-noted objectives as well as additional advantages are provided in the inventive apparatus which includes a carrier device for carrying an implantable hearing aid actuator at a first end, and a swivel device for pivotably supporting the carrier device. Such pivotable support allows the first-end of the carrier device to be laterally pivotable in first and second dimensions relative to the swivel device. The apparatus further includes a mounting device for mounting the apparatus to a patient's skull, wherein the swivel device may be secured to the mounting device.

In one aspect of the present invention the swivel device is provided in a unitary fashion. That is, the swivel device is selectively positionable relative to and otherwise securable to the mounting device as a single unit. Such an arrangement simplifies installation procedures in conjunction with hearing aid implants. Further, to enhance actuator depth positioning, the carrier device and swivel device are preferably adapted to allow the carrier device to be selectively positioned in a third dimension relative to the swivel device.

Preferably, the unitary swivel device includes interconnected, opposing first and second holder members with a pivot member (e.g., a rotatable ball) captured between the first and second holder members. The pivot member may include an opening for supportably receiving the carrier device, wherein the carrier device is slidably positionable in the opening along a linear continuum of positions in the third dimension. As may be appreciated, pivotable movement of the carrier device will effect corresponding rotation of the pivot member relative to the interconnected first and second holder members.

In the later regard, the first and second holder members may be interconnected to permit a limited range of relative movement therebetween, thereby facilitating selective rotation of the pivot member upon pivotable movement of the carrier device. Relatedly, the inventive apparatus may further comprise a locking member interconnectable to the mounting device to selectively apply a compressive force to and thereby restrict relative movement between the first and second holder members, wherein a selected angular orientation between the carrier device and the mounting device may be maintained by the locking member.

Further, the locking member may also be employable to lock-in a selected linear position of the carrier device relative to the swivel device. More particularly, the pivot member may include a plurality of slits extending through an upper portion thereof to define a plurality of separated, upper portions of the pivot member. Correspondingly, the first holder member may comprise an aperture sized for contact positioning about the slitted portion of the pivot member. Consequently, when the locking member is interconnected to the mounting device to apply a compressive force to the first and second holders, such force will effect inward movement of the plurality of separated, upper portions to restrictably engage the carrier device.

In another aspect of the present invention, the carrier device may be interconnected to the swivel device in a manner that allows for selective advancement of the carrier device relative to the swivel device, wherein a first degree of actuator depth positioning latitude is provided; and, the carrier device may comprise at least a first carrier member and an interconnected second carrier member having a distal end connectable to an actuator, wherein the second carrier member is selectively advancable relative to the first carrier member to yield a second degree of depth positioning latitude. Such multiple depth positioning functionality not only facilitates accurate placement of an implantable hearing aid actuator but also facilitates a greater depth positioning range for an increased range of patient applications. In one arrangement, the first and second carrier members may be disposed coaxially and interconnected for selective, telescoping advancement of the second carrier member relative to the first carrier member.

Preferably, the first and second carrier members may be threadably interconnected, wherein driven rotation of the first carrier member effects a predetermined degree of linear travel by the second carrier member. In this regard, the swivel device may include an opening for supportably receiving the carrier device, wherein a top end of the first carrier member projects from the swivel device to provide ready access for driven rotation by an accessory tool.

In addition to first and second carrier members, the carrier device may further include a third carrier member, rotatably interconnected to the first carrier member, for restricting rotational movement of the second carrier member. In one arrangement, the second carrier member may include a linear slot while the third carrier member includes a projecting retention pin positioned within the slot of the second carrier member. As such, when the third carrier member is rotationally fixes (e.g., via use of a locking member as noted above) and the first carrier member is rotated, the third carrier member restricts rotation of the second carrier member, thereby causing the second carrier member to telescope away from both of the first and third carrier members.

In one embodiment, a mounting device is provided which includes a cylindrical barrel portion for supportably receiving a swivel device and carrier device interconnected thereto. The barrel portion includes a bottom end plate and is internally threaded, wherein the swivel device may be "locked-in" between an externally threaded locking member and the bottom end plate. The swivel device may include interconnected, top and bottom plate members with opposing central apertures having beveled edge surfaces for receiving a round pivot member therebetween. The pivot member is provided with a central opening therethrough for slidably receiving an outer support member of the carrier device. The carrier device further includes an internal shaft member rotatably interconnected at a top end to a top end of the outer support member, and interconnected at a bottom end to a telescoping member. In turn, a distal end of the telescoping member is interconnected to an electromechanical transducer actuator.

The entire carrier device may be selectively located at one of a linear continuum of positions relative to the swivel device to provide a first measure of depth positioning control. Further, the carrier device may be pivoted relative to the mounting device to provide for lateral positioning of the electromechanical transducer actuator. When a desired depth and angular orientation of the carrier device is established, such position may be "locked-in" by tightening the locking ring down on the swivel assembly. Then, the telescoping member of the carrier device may be selectively advanced to position the electromechanical transducer actuator in a desired contact position with the ossicular chain (e.g., contact with the incus bone) or oval window.

In view of the foregoing, it will apparent that an inventive method for positioning an implantable hearing aid actuator is also provided. The inventive method includes the steps of attaching a mounting device to a patient's skull and supporting a swivel device on the mounting device, wherein the swivel device pivotably supports a carrier device having an implantable hearing aid actuator interconnected thereto. The method further provides for the positioning of the carrier device so as to locate the implantable hearing aid actuator at a desired location within the patient's skull.

Preferably, the supporting step is achieved via the placement of the swivel device as a single unit into a support position on the mounting device. In one embodiment, this may be achieved by inserting the swivel device as a unit into a barrel portion of the mounting device and supportably engaging a bottom end plate of the barrel portion.

The positioning step of the inventive method preferably includes the sub-steps of pivoting the carrier device and interconnected implantable hearing aid actuator into a desired angular orientation relative to the mounting device within a patient's skull, and advancing the carrier device relative to the swivel device. Further, in an arrangement where the carrier device includes at least first and second carrier members, the positioning step may further include the sub-step of advancing the second carrier member relative to the first carrier member.

When an electromechanical transducer actuator is utilized, a desired contact location may be defined on the ossicular chain (e.g., the incus bone) or oval window within a patient's skull, wherein a probe tip of the electromechanical transducer actuator is brought into gradual contact with the contact location during positioning. In this regard, the inventive method may further provide for advancing the second carrier member relative to the first carrier member so as to provide a predetermined degree of loading by the probe tip on the contact location.

Numerous additional aspects and advantages of the present invention will become apparent to those skilled in the art upon consideration of further description that follows.

DETAILED DESCRIPTION

The invention will now be further described with reference to the mounting apparatus embodiment 10 illustrated in FIG. 1. Such description is for purposes of facilitating an understanding of the invention and other embodiments will be apparent to those skilled in the art.

The mounting apparatus 10 includes a carrier assembly 20, a swivel assembly 40, and a mounting assembly 60. Such assemblies may be readily interconnected and disposed to cooperate in a manner that allows for selective, three-dimensional positioning of an implantable hearing aid actuator, such as exemplary actuator 80, at a desired location within a patient's skull.

By way of general overview, the exemplary actuator 80 may be supportably connected to a first end 22 of the carrier assembly 20. In turn, the carrier assembly 20 may be supportably received in an opening 42 provided in the swivel assembly 40 and the assembled carrier assembly 20/swivel assembly 40 may be supportably interconnected to a mounting apparatus 62 attached to a patient's skull (e.g. via the insertion of skull attachment devices 70 through apertures 65 of mounting legs 63 into the skull). As will be further described, the interconnection between carrier assembly 20 and swivel assembly 40 provides for pivotable, lateral positioning of the first end 22 of the carrier assembly 20, and of the actuator 80 interconnected thereto. Further, carrier device 20 and swivel assembly 40 may be provided so that carrier assembly 20 may be selectively secured along a continuum of positions within the opening 42 of the swivel assembly 40, thereby facilitating advancement/retraction of the carrier assembly 20 and interconnected actuator 80, in a depth dimension. Additionally, the carrier assembly 20 may be defined so that its first end 22 may be selectively advanced/retracted in the depth dimension relative to an outer support member 24 thereto.

Figure 1:
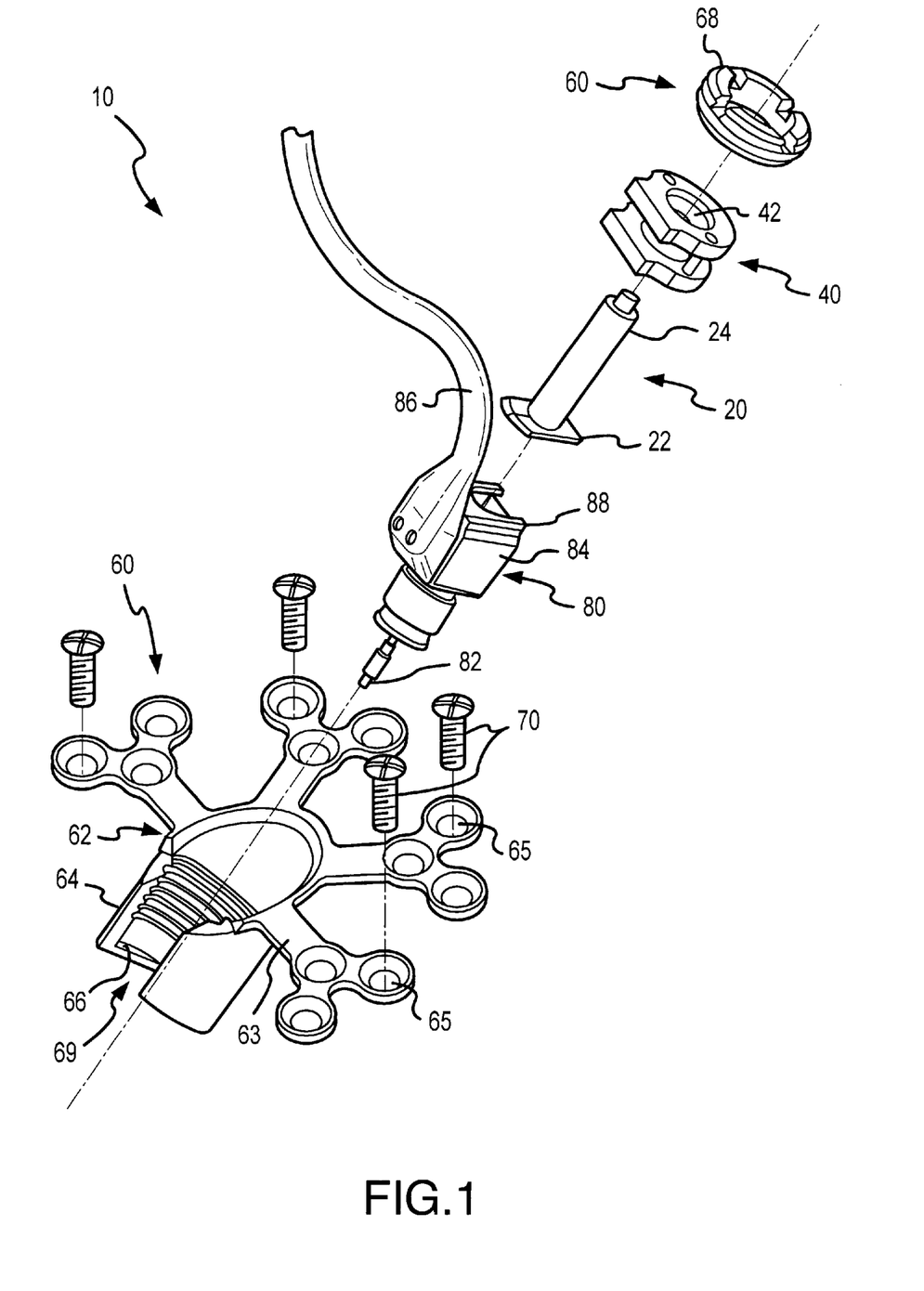
FIG. 1 is an exploited view of one embodiment of an inventive apparatus for supportably positioning an implantable hearing aid actuator within a patient's skull.

As illustrated in FIG. 1, swivel assembly 40 may be provided in a unitary, or interconnected, form so that it may be readily positioned about the outer support member 24 of carrier assembly 20, thereby facilitating positioning and interconnection of the swivel assembly 40 within the mounting apparatus 62. In the later regard, it should be noted that in the illustrated embodiment swivel assembly 40 is configured for mating receipt in a predetermined orientation by a complimentarily configured barrel portion 64 of mounting apparatus 62. Further, unitary swivel assembly 40 is sized to supportably rest upon an end plate portion 66 of mounting apparatus 62. As will be further described, when carrier assembly 20 has been advanced/retracted and pivoted to be in a desired linear and angular position, a locking member 68, positionable within a top end of the barrel 64 of mounting apparatus 62, may be tightened against the top of swivel assembly 40 to "lock-in" the desired linear and angular position of carrier assembly 20.

To facilitate such functionality, one embodiment of swivel assembly 40 will now be discussed in detail with reference to FIGS. 2A–2D. As illustrated, swivel assembly 40 includes opposing, top and bottom plate members 44a and 44b, respectively, which are interconnected to capture a rotatable ball member 46 therebetween. In particular, the top and bottom plate members 44a, 44b include centrally aligned apertures 45a, 45b, with opposing beveled, ring-shaped, edge surfaces 41a, 41b, wherein the ball member 46 is seated between the beveled surfaces 41a and 41b. The rotatable ball member 46 also includes an aperture 47 there through which, together with apertures 45a, 45b, collectively define the opening 42 of swivel assembly 40. In this regard, aperture 47 may be sized to slidably receive the outer support member 24, yet restrain free relative movement therebetween. As will be appreciated, when carrier assembly 20 is positioned through opening 42, pivotal movement of the carrier assembly 20 will cause rotation of the ball member 46. In relation to such movement, apertures 45a, 45b are sized larger than aperture 47 so as to permit pivotal movement of carrier assembly 20 within a predetermined range of motion. By way of example, swivel assembly 20 may be provided so as to permit carrier assembly 20 to pivot up to 30° about and relative to a center axis passing through the apertures 45a and 45b.

Figure 2A:
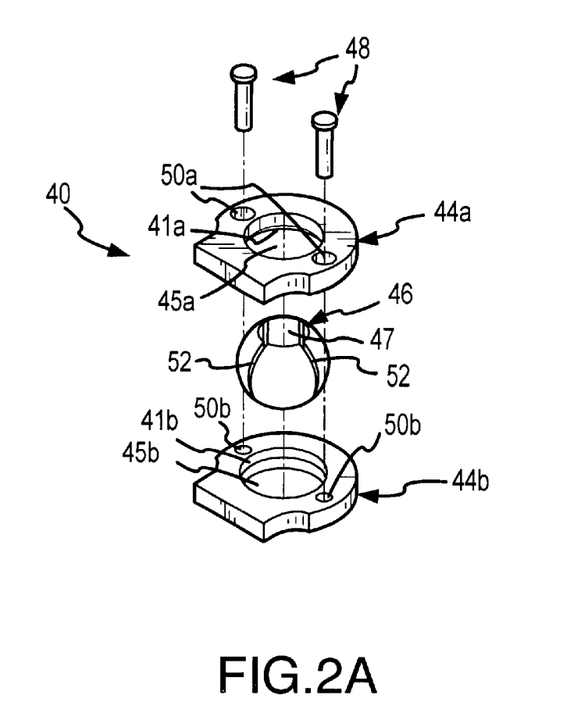
FIGS. 2A, 2B, 2C and 2D illustrate an exploded view, an assembled side view, and two cross-sectional side views (i.e., taken along cross-section line AA of FIG. 2B), respectively, of a swivel assembly embodiment shown in the embodiment of FIG. 1.
Figure 2B:
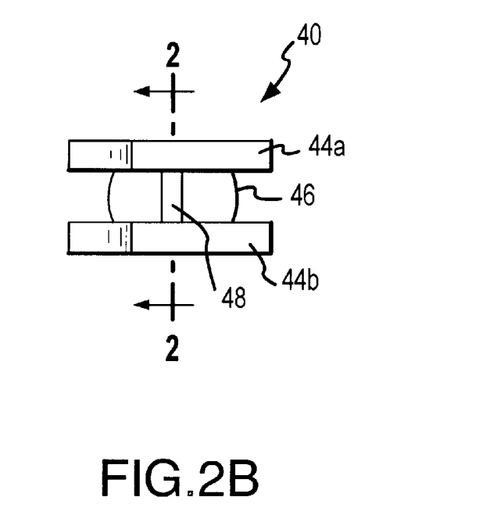
Figure 2C:
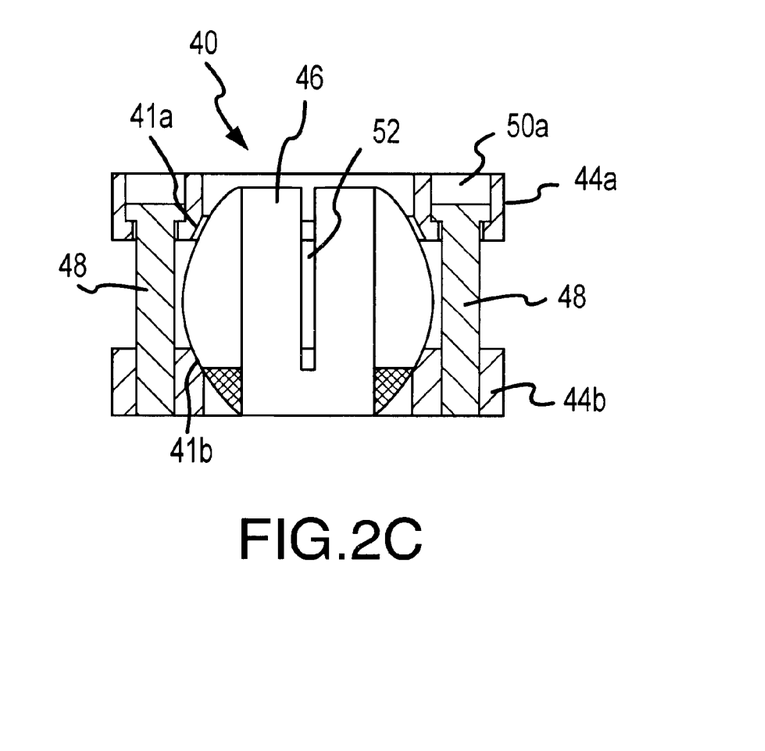
Figure 2D:
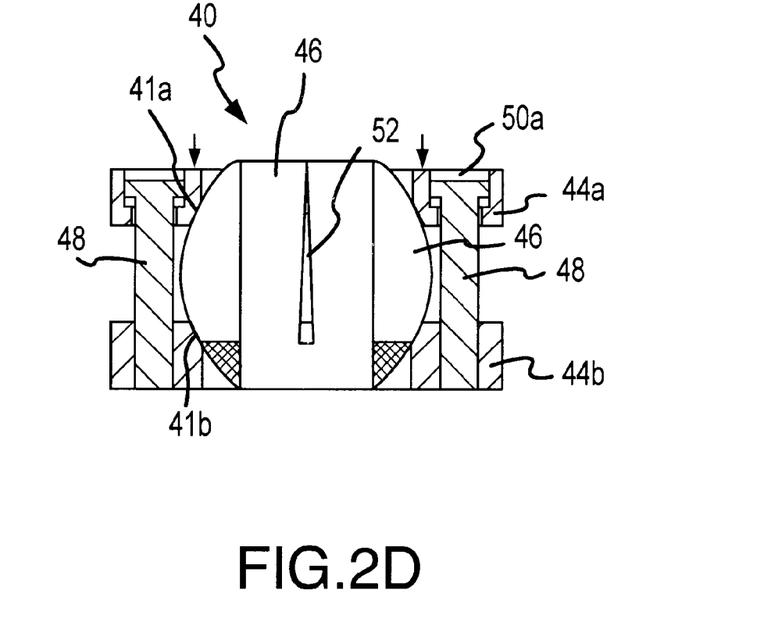

The top and bottom plate members 44a and 44b are interconnected by headed pins 48 which are inserted through apertures 50a and 50b of the top and bottom plate members 44a and 44b, respectively. The apertures 50b defined in the bottom plate member 44b are sized for retentive press-fit receipt of the bottom ends of headed pins 48. On the other hand, the apertures 50a defined in top plate member 44a are sized relative to the headed pins 48 to permit a small degree of linear travel therebetween (e.g., about 0.01"), thereby allowing the ball member 46 to rotate relative to the top and bottom plate members 44a and 44b, absent the application of a compressive force on the swivel assembly 40. For purposes of illustrating the rotatability/lockability of ball member 46, FIGS. 2C and 2D illustrate swivel assembly 40 with the top plate member 44a in a "lifted" position and in a "compressed" position, respectively.

In the later regard, and as noted above in relation to the embodiment of FIG. 1, a locking member 68 may be provided to apply a force to the top plate member 44a to lock-in a desired linear and angular disposition of the carrier assembly 20 shown in FIG. 1. For such purposes, rotatable ball member 46 includes four slits 52 which extend from aperture 47 through a top portion of the ball member 46 to define four slightly separated upper sections. Of importance, slits 52 extend through only a portion of the rotatable ball member 46. Consequently, and as shown by FIG. 2D, upon the application of a force to the top surface of the top plate member 44a (e.g., by the locking member 68 as described above), the beveled surface 41a of the top plate member 44a will act to apply on inward force about a top end of the ball member 46 so as to urge the four upper sections thereof inwards. As such, when carrier assembly 20 is positioned within the opening 42 of swivel assembly 40, the inward motion of the top sections of ball member 46 may serve to lock-in a given linear position of the carrier assembly 20 relative to the swivel assembly 40. Further, upon the application of downward force to the top plate member 44a, beveled, annular surface 41a of the top plate member 44a will act to apply downward forces about the contacted ring portion of ball member 46, thereby serving to lock-in a given rotational orientation of ball member 46 relative to the top and bottom plate members 44a, 44b. As noted above, when carrier assembly 20 is positioned in the opening 42 of swivel assembly 42 the ability to lock-in a given rotational orientation of ball member 46 allows the carrier assembly 20 to be set in a desired angular position.

Figure 3A:
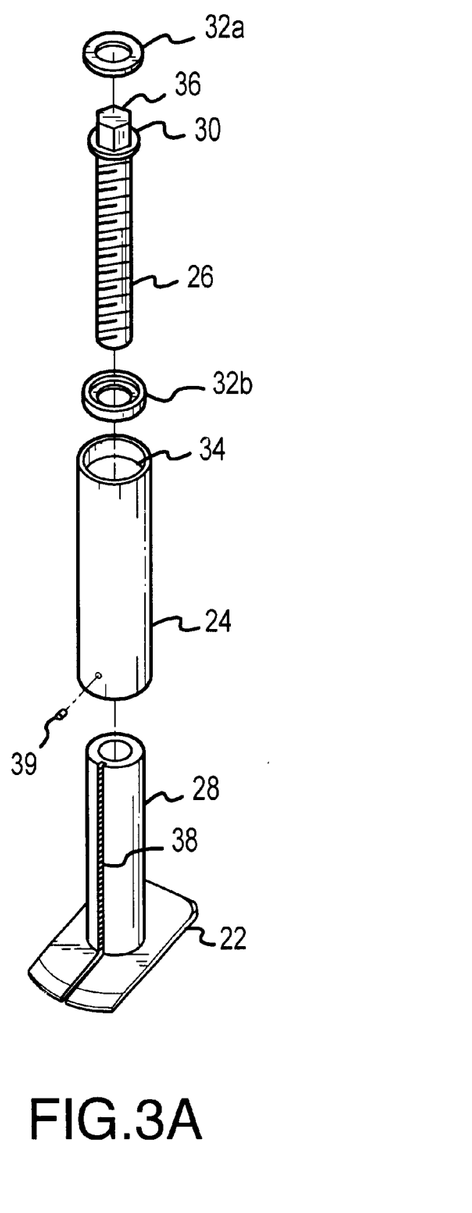
FIGS. 3A, 3B and 3C illustrate an exploded view, an assembled top view and a cross-sectional side view (i.e., taken along cross-section line AA of FIG. 3B), respectively, of a carrier assembly embodiment shown in the embodiment of FIG. 1.
Figure 3B:
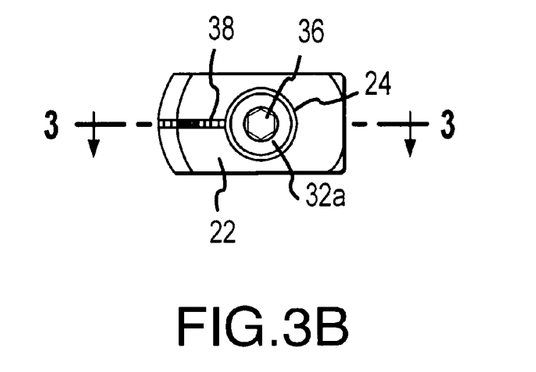
Figure 3C:
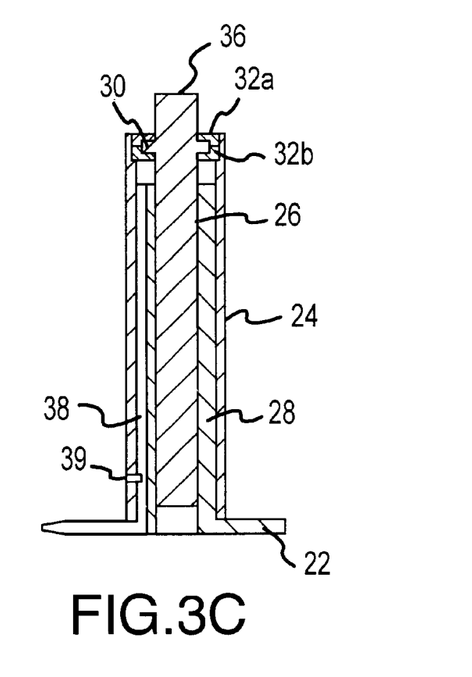

Reference will now be made to FIGS. 3A–3C which illustrate one embodiment of the carrier assembly 20 shown in FIG. 1. The illustrated carrier assembly 20 includes an outer support member 24, an inner shaft member 26 and an extendable, or telescoping, shaft member 28 having a foot-like configuration which defines the first end 22 of the carrier assembly 20. In the illustrated embodiment, inner shaft member 26 is threaded for driven engagement with an internally threaded surface within telescoping support member 28. In this regard, a ring portion 30 is provided at the top end of the internal shaft 26 and is sized for rotatable positioning in a bushing arrangement defined by top and bottom ring members 32a, 32b. More particularly, the top and bottom ring members 32a, 32b may be interconnected about their annular peripheries so as to capture the ring portion 30 of the internal shaft member 26, and the adjoined rings 32a, 32b may be secured within a top end 34 of the outer tube member 24. Such an arrangement axially fixes internal shaft member 26 relative to the outer support member 24, but allows the internal shaft member 26 to be rotated relative to the outer support member 24, e.g., via driven engagement by an accessory tool with a hex-end 36 provided at the top end of the internal shaft member 26.

As noted, telescoping support member 28 may be provided with an internally threaded surface for threaded engagement with the inner shaft member 26. Further, telescoping support member 28 may include an outer groove 38 extending along the length of the telescoping support member 28. Such groove 38 is provided to co-act with a restraining member 39 projecting from the outer support member 24. More particularly, when outer support member 24 is in a locked position as described above, restraining member 39 acts to restrain telescoping support member 28 from rotation relative to outer support member 24 upon driven rotation of inner shaft 24. As such, upon driven rotation of inner shaft member 26, the telescoping support member 28, and an implantable actuator 80 interconnected to the footed first end 22 thereof, may be selectively advanced/retracted relative to the outer support member 24 and inner shaft member 26.

Figure 4:
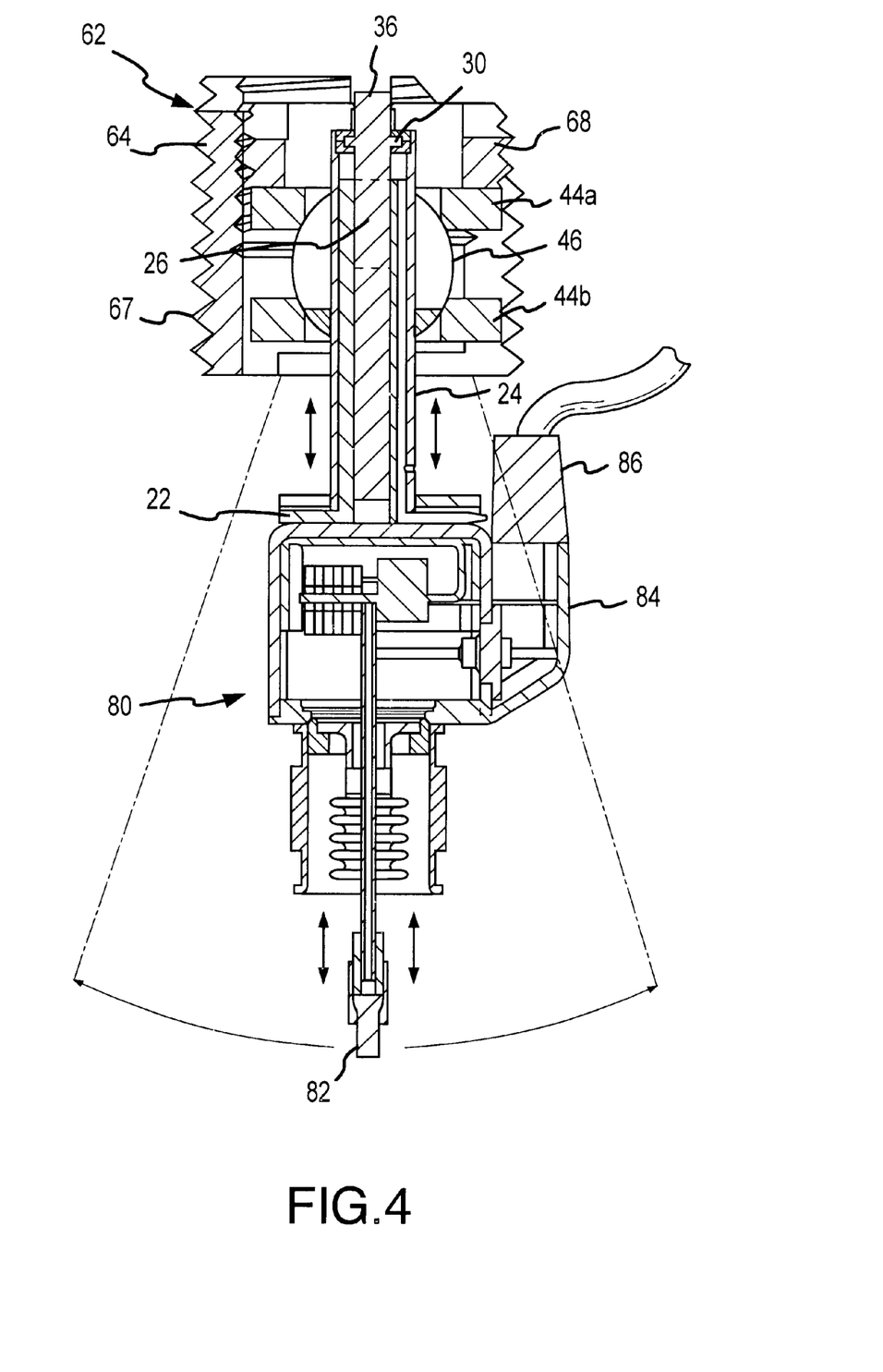
FIG. 4 is a cross-sectional view of the various components illustrated in FIG. 1 interconnected for use.
Figure 5:
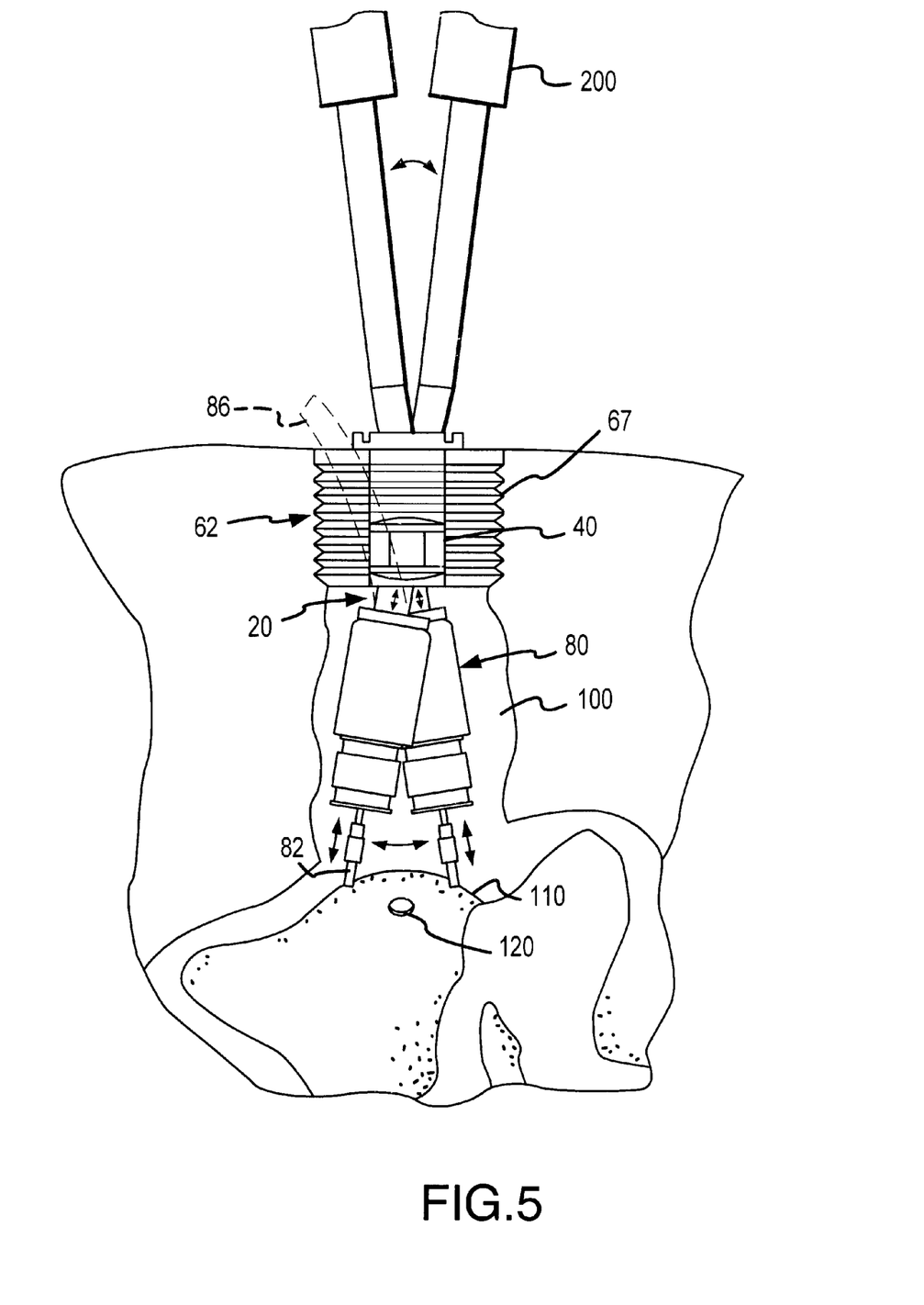
FIG. 5 illustrates positioning of the various components shown in FIG. 1 during an exemplary implant procedure.

Referring now to FIGS. 1, 4 and 5, interconnection and use of the various components in one application of the described embodiment will be reviewed. Initially, and as shown in FIG. 5, an opening 100 in the mastoid process of a patient's skull may be defined by drilling or other appropriate process. The opening 100 should be of size sufficient to accommodate insertion of a cylindrical barrel portion 64 of the mounting apparatus 62 therethrough. In this regard, FIG. 1 illustrates a mounting assembly 60 for which skull attachment of the mounting apparatus 62 is achieved via the use of attachment devices 70 inserted through apertures 65 provided in radiating mounting legs 63 at the top end of the mounting apparatus 62. In an alternate embodiment, as shown in FIGS. 4 and 5, the cylindrical barrel portion 64 may be provided with external threads 67 for threaded engagement with a tapped bore portion defined within the opening 100 of a patient's skull.

After securement of the mounting apparatus 62 to a patient s skull, various components of the positioning embodiment 10, together with an interconnected actuator 80, may be positioned through the mounting apparatus 62. In this regard, interconnection of the various components of the positioning assembly 10, as well as interconnection of the positioning assembly 10 to actuator 80, may be completed in conjunction with an implant procedure, or alternatively, may be at least partially completed as part of a production/assembly operation prior to shipment. In either case, before positioning within the mounting apparatus 62, footed first end 22 of telescoping support member 28 of the carrier assembly 20 may be slidably disposed within a channel 88 provided at the top end of actuator 80 a body portion 84, and swivel assembly 40 may be positioned as a unit about the outer support member 24 of the carrier assembly 20. In the later regard, and as noted above, the opening 42 defined through swivel assembly 40 may be sized for slidable friction fit with the outside surface of the support member 24 so as to allow for slidable relative positioning between the two, as well as a degree of retention that restricts swivel assembly 40 from simply sliding off the carrier assembly 20.

In positioning the interconnected positioning assembly 10 and actuator 80 within the mounting apparatus 62, it may be noted that tab-like extensions of the top and bottom plate members 44a, 44b of the swivel assembly 40, as well as rectangular portions of the footed first end 22 and actuator 80, as well as a signal transmission cable 86 comprising actuator 80, may all be aligned relative to a complimentary opening 69 provided along one side of the barrel portion 64 of the mounting apparatus 62. The interconnected positioning assembly 10 and actuator 80 may then be linearly advanced through the barrel portion 64 of mounting apparatus 62 until the bottom plate member 44b of swivel assembly 40 supportably engages the bottom end plate 66 of the mounting apparatus 62. Then, the locking ring 68 may be located in the top end of the barrel portion 64, but not yet tightened against swivel assembly 40. The positioning apparatus 10 is now disposed for selective positioning of actuator 80.

In particular, an accessory tool 200 may be inserted through an aperture in locking ring 68 to engage the hex-end 36 of the internal shaft member 26 of carrier assembly 20. Using the accessary tool 200 the hearing aid actuator 80 may be selectively advanced/retracted into a preliminarily desired depth position via slidable advancement/retraction of the outer support member 24 of the carrier assembly 20 within the opening 42 of the swivel assembly 40. Further, the angular orientation of the actuator 80 may be selectively adjusted via use of the accessory tool 200 to effect pivotal movement of the carrier assembly 20 and rotation of ball member 46 relative to the top and bottom plate members 44a, 44b of the swivel assembly 40.

In this regard, where actuator 80 comprises an electromechanical transducer (e.g. as shown in FIGS. 1, 4 and 5), a probe tip 82 of the actuator 80 may be pivoted into a position where it is directed towards a desired contact location 120 on the incus bone 110. Further in this regard, prior to insertion of the positioning apparatus 10 through mounting apparatus 60, a small hole may be defined at the desired contact location 120 on the surface of the incus 110 (e.g., via use of a laser guide arrangement). It should be noted that the contact location may be defined on other ossicular bones or even perhaps the oval window.

When the probe tip 82 of the electromechanical transducer actuator 80 is angularly directed towards the desired contact location 120, the locking ring 68 may be further advanced within the barrel portion 64 of the mounting apparatus 60 so as lock in the set angular orientation and depth setting of the carrier assembly 20. Then, to achieve precise positioning of the probe tip 82 a further accessory tool (not shown) may be inserted through the aperture of the mounting/locking ring 68 to natingly engage the hex-end 36 of the internal shaft member 26 of the carrier assembly 20 for driven rotation thereof. In this regard, it should be appreciated that the threading provided on the internal shaft member 26 and telescoping shaft member 28 may be defined so that, for a given amount of driven rotation of the hex-end 36, a corresponding predetermined desire of linear travel by the first end 22 of the telescoping shaft member 28 will be affected (e.g., ¼ mm travel for each complete rotation). As such, after the probe tip 82 has been advanced into initial contact with the incus 110, a predetermined degree of loading may be selectively established by driven rotation of hex-end 36, a predetermined number of revolutions. As will be appreciated, the ability to achieve precise positioning, and loading of an actuator 80 relative to the ossicular chain, yields enhanced acoustic signal transmission and overall improved hearing aid performance. After positioning of the actuator 80, placement of and connections between other implanted components of a given hearing aid system may be completed prior to system testing and surgical sew-up.

The description provided above is solely for purposes of facilitating an understanding of one embodiment of the present invention. Additional embodiments will be apparent to those skilled in the art. For example, while the embodiment described may employ an electromechanical transducer actuator 80, aspects of the present invention are also employed for positioning other types of implantable hearing aid actuators. Such alternative applications as well as modifications and adaptations of the described embodiment are intended to be within the scope of the present invention as defined by the claims which follow.

What is claimed is:

1. An apparatus for supportably positioning an implantable hearing aid actuator within a patients skull, comprising:

a carrier device for carrying an implantable hearing aid actuator at a first-end of said carrier device, wherein said first-end of said carrier device is pivotable in first and second dimensions;

a mounting device for mounting said apparatus to a patient's skull;

a pre-assembled unitary swivel device for pivotably supporting said carrier device relative to said mounting device, comprising:

interconnected, opposing first and second holder members; and a pivot member captured between said first and second holder members; wherein said swivel device is selectively securable as a single unit to said mounting device.

2. An apparatus as recited in claim 1, wherein said carrier device is selectively positionable in a third dimension relative to said swivel device.

3. An apparatus as recited in claim 1, wherein said pivot member includes an opening for supportably receiving said carrier device.

4. An apparatus as recited in claim 3, wherein said carrier device is slidably positionable in said opening along a continuum of positions in said third dimension.

5. An apparatus as recited in claim 4, wherein said first and second holder members are interconnected to permit relative movement therebetween.

6. An apparatus as recited in claim 5, further including: a locking member interconnectable to said mounting device to selectively restrict said relative movement between said first and second holder members, wherein a selected angular orientation between said carrier device and said mounting device is maintainable by said locking member.

7. An apparatus as recited in claim 6, wherein said pivot member comprises a plurality of slits extending through a portion thereof to define a plurality of separated, upper portions of the pivot member, and wherein said locking member is interconnectable to said mounting device to effect inward movement of said upper portions of said pivot member and thereby restrictably engage said carrier member in a selected one of said continuum of positions.

8. An apparatus as recited in claim 2, wherein said carrier device comprises:

a first carrier member; and a second carrier member supportably interconnected to and selectively advancable in said third dimension relative to said first carrier member.

9. An apparatus as recited in claim 8, wherein said first and second carrier members are disposed coaxially and interconnected for selective, telescoping advancement and retraction of said second carrier member relative to said first carrier member.

10. An apparatus for supportably positioning an implantable hearing aid actuator within a patient's skull, comprising:

a carrier device for carrying an implantable hearing aid actuator at a first end of said carrier device, said carrier device including a first carrier member and a second carrier member supportably interconnected to and selectively advancable relative to said first carrier member in a first dimension;

a swivel device for pivotably supporting said carrier device, wherein said first and second carrier members of said carrier device are linearly advancable together in said first dimension relative to said swivel device, and wherein said first end of said carrier device is pivotable in second and third dimensions relative to said swivel device; and a mounting device for supporting said swivel device and mounting said apparatus to a patient's skull.

11. An apparatus as recited in claim 10, wherein said first and second carrier members are disposed coaxially and interconnected for selective, telescoping advancement and retraction of said second carrier member relative to said first carrier member.

12. An apparatus as recited in claim 10, wherein said first and second carrier members are threadably interconnected, and wherein driven rotation of said first carrier member effects a predetermined degree of linear travel by said second carrier member.

13. An apparatus as recited in claim 10, said carrier device further comprising:

a third carrier member rotatably interconnected to said first carrier member, for direct engagement with said swivel device and for restricting rotational movement of said second carrier member.

14. An apparatus as recited in claim 13, wherein said second carrier member includes a linear slot, and wherein said third carrier member includes a projecting restraining member pin positioned within said slot of said second carrier member.

15. An apparatus as recited in claim 14, wherein said swivel device includes:

interconnected, opposing first and second holder members; and a pivot member captured between said first and second holder members and having an opening therethrough for slidable, direct engagement with said third carrier member.

16. A method for supportably positioning an implantable hearing aid actuator within a patient's skull, comprising:

attaching a mounting device to a patient's skull;

supporting a pre-assembled swivel device comprising a pivot member captured between interconnected opposing first and second holder members as a single unit on said mounting device, wherein said swivel device pivotably supports a carrier device having an implantable hearing aid actuator interconnected to a first-end thereof; and positioning said carrier device to locate said implantable hearing aid actuator at a desired location within said patient's skull.

17. A method as recited in claim 16, said positioning step including:

pivoting said carrier device and interconnected implantable hearing aid actuator into a desired angular orientation relative to said mounting device within said patient's skull; and first advancing said carrier device relative to said swivel device.

18. A method as recited in claim 17, wherein said carrier device includes a first carrier member and a second carrier member supportably interconnected to said first carrier member, and wherein said positioning step further includes:

second advancing said second carrier member relative to said first carrier member.

19. A method as recited in claim 18, wherein said implantable hearing aid actuator comprises an electromechanical transducer having a probe tip, wherein said desired location is on an ossicular bone within said patient's skull, and wherein said probe tip is advanced in said second advancing step to contact said ossicular bone at the predetermined location.

20. An apparatus for supportably positioning an implantable hearing aid actuator within a patients skull, comprising:

a carrier device for carrying an implantable hearing aid actuator at a first-end of said carrier device;

a mounting device for mounting said apparatus to a patient's skull;

a unitary swivel device pivotably supporting said carrier device, wherein said swivel device is selectively securable as a single unit with said carrier device to said mounting device, said swivel device comprising:

a pivot member that includes a plurality of slits extending through a portion thereof to define a plurality of separated upper portions of the pivot member, and a locking member interconnectable to said mounting device to effect inward movement of said upper portions of said pivot member and thereby restrictably engage said carrier member in said swivel device.

21. An apparatus as recited in claim 20, wherein said first-end of said carrier device is pivotable in first and second dimensions with said swivel device and said carrier device is selectively positionable in a third dimension relative to said swivel device.

22. An apparatus as recited in claim 21, wherein said swivel device includes interconnected, opposing first and second holder members, and wherein the pivot member is captured between said first and second holder members.

23. An apparatus as recited in claim 22, wherein said pivot member includes an opening for supportably receiving said carrier device.

24. An apparatus as recited in claim 23, wherein said carrier device is slidably positionable in said opening along a continuum of positions in said third dimension.

25. An apparatus as recited in claim 24, wherein said first and second holder members are interconnected to permit relative movement therebetween.

26. An apparatus as recited in claim 25, wherein said locking member is interconnectable to said mounting device to selectively restrict said relative movement between said first and second holder members, wherein a selected angular orientation between said carrier device and said mounting device is maintainable by said locking member.

27. An apparatus as recited in claim 21, wherein said carrier device comprises:

a first carrier member; and a second carrier member supportably interconnected to and selectively advancable in said third dimension relative to said first carrier member.

28. An apparatus as recited in claim 27, wherein said first and second carrier members are disposed coaxially and interconnected for selective, telescoping advancement and retraction of said second carrier member relative to said first carrier member.

29. An apparatus for supportably positioning an implantable hearing aid actuator within a patient's skull, comprising:

a carrier device for carrying an implantable hearing aid actuator at a first end of said carrier device, said carrier device comprising:

a first carrier member;

a second carrier member including a linear slot disposed therein, wherein the second carrier member is supportably interconnected to and selectively advancable relative to said first carrier member in a first dimension;

a third carrier member rotatably interconnected to said first carrier member and including a projecting restraining pin positioned within the linear slot of said second carrier member; and a swivel device pivotably supporting said carrier device along a continuum of positions, wherein said carrier device is linearly advancable in said first dimension relative to said swivel device, and wherein said carrier device is pivotable in second and third dimensions relative to said swivel device; and a mounting device for supporting said swivel device and mounting said apparatus to a patients skull.

30. An apparatus as recited in claim 29, wherein said first and second carrier members are disposed coaxially and interconnected for selective, telescoping advancement and retraction of said second carrier member relative to said first carrier member.

31. An apparatus as recited in claim 29, wherein said first and second carrier members are threadably interconnected, and wherein driven rotation of said first carrier member effects a predetermined degree of linear travel by said second carrier member.

32. An apparatus as recited in claim 29, wherein said third carrier member is rotatably interconnected to said first carrier member, for direct engagement with said swivel device and for restricting rotational movement of said second carrier member.

33. An apparatus as recited in claim 29, wherein said swivel device comprises:

interconnected, opposing first and second holder members; and a pivot member captured between said first and second holder members and having an opening therethrough for slidable, direct engagement with said third carrier member.

34. A method for positioning an implantable hearing aid actuator within a patient's skull, comprising:

attaching a mounting device to a patient's skull;

supporting a swivel device relative to said mounting device, wherein said swivel device pivotably supports a carrier device having an implantable hearing aid actuator interconnected thereto;

positioning said carrier device to locate said implantable hearing aid actuator at a desired location within said patient's skull, said positioning step comprising the steps of:

first, advancing said carrier device in a first dimension relative to said swivel device, wherein said carrier device includes a first carrier member interconnected to a second carrier member; and second, further advancing the second carrier member of the carrier device in the first dimension relative to the first carrier member of the carrier device and the swivel device.

35. A method as recited in claim 34, said positioning step including:

pivoting said carrier device and interconnected implantable hearing aid actuator into a desired angular orientation relative to said mounting device within said patient's skull, wherein said pivoting step occurs before said first, advancing said carrier device step.

36. A method as recited in claim 34, wherein said swivel device comprises a pivot member captured between interconnected opposing first and second holder members and said supporting step comprises supporting said swivel device as a single unit relative to said mounting device.

37. A method as recited in claim 18, wherein said implantable hearing aid actuator comprises an electromechanical transducer having a probe tip, wherein said desired location is on an ossicular bone within said patient's skull, and wherein said probe tip is advanced in said second advancing step to contact said ossicular bone at the predetermined location.

* * * * *